(12) United States Patent
Kuhman et al.

(10) Patent No.: US 7,134,316 B2
(45) Date of Patent: Nov. 14, 2006

(54) APPARATUS AND METHOD FOR DETERMINING FEEDSCREW AND BARREL WEAR

(75) Inventors: Jeffrey A. Kuhman, Tecumseh, MI (US); Richard T. Harris, Britton, MI (US)

(73) Assignee: Kuhman Investment Co., LLC, Tecumseh, MI (US)

( * ) Notice: Subject to any disclaimer, the term of this patent is extended or adjusted under 35 U.S.C. 154(b) by 0 days.

(21) Appl. No.: 10/965,649

(22) Filed: Oct. 14, 2004

(65) Prior Publication Data

US 2006/0081030 A1    Apr. 20, 2006

(51) Int. Cl.
G01N 3/56    (2006.01)
G01N 3/62    (2006.01)

(52) U.S. Cl. .............................. 73/7; 277/317; 277/321

(58) Field of Classification Search ...................... 73/7; 277/317, 321
See application file for complete search history.

(56) References Cited

U.S. PATENT DOCUMENTS

| | | | |
|---|---|---|---|
| 3,932,941 A * | 1/1976 | Ormsby ............................ 73/7 |
| 4,197,070 A | 4/1980 | Koschmann | |
| 4,272,466 A | 6/1981 | Harris | |
| 4,382,253 A * | 5/1983 | Belthle ........................ 340/680 |
| 4,494,877 A | 1/1985 | Upmeier et al. | |
| RE31,903 E | 6/1985 | Faillace | |
| 4,604,251 A | 8/1986 | Kuhman ..................... 264/408 |
| 4,685,488 A | 8/1987 | Corbin et al. | |
| 4,775,130 A | 10/1988 | Von Holdt | |
| 5,051,415 A | 9/1991 | Morgan et al. | |
| 5,116,135 A | 5/1992 | Kaiser et al. | |
| 5,135,378 A | 8/1992 | Catton | |
| 5,246,643 A | 9/1993 | Inaba et al. | |
| 5,542,835 A | 8/1996 | Kennedy et al. | |
| 5,794,940 A | 8/1998 | Brueggmann | |
| 5,887,655 A | 3/1999 | Haugen et al. | |
| 6,306,319 B1 | 10/2001 | Swain et al. | |
| 6,481,996 B1 | 11/2002 | Graham | |
| 6,592,354 B1 | 7/2003 | Kachnic et al. | |
| 6,741,074 B1 | 5/2004 | DeBlock et al. | |
| 2003/0066215 A1 | 4/2003 | Grant | |

* cited by examiner

*Primary Examiner*—Daniel S. Larkin
(74) *Attorney, Agent, or Firm*—Butzel Long

(57) ABSTRACT

An apparatus and a method for determining wear of a feedscrew and barrel combination includes a measuring aperture formed in a wall of the barrel, a gage plug releasably retained in the measuring aperture and having an inner end curved to correspond to a curvature of a surface of the central bore surrounding an inner end of the measuring aperture, and a retaining plug releasably retained in the measuring aperture for maintaining the gage plug in place. When the plugs are removed, the gage plug can be measured for barrel wear and a probe can be inserted into the measuring aperture for determining feedscrew wear. A test bar simulating feedscrew wear is used to calibrate the probe.

16 Claims, 8 Drawing Sheets

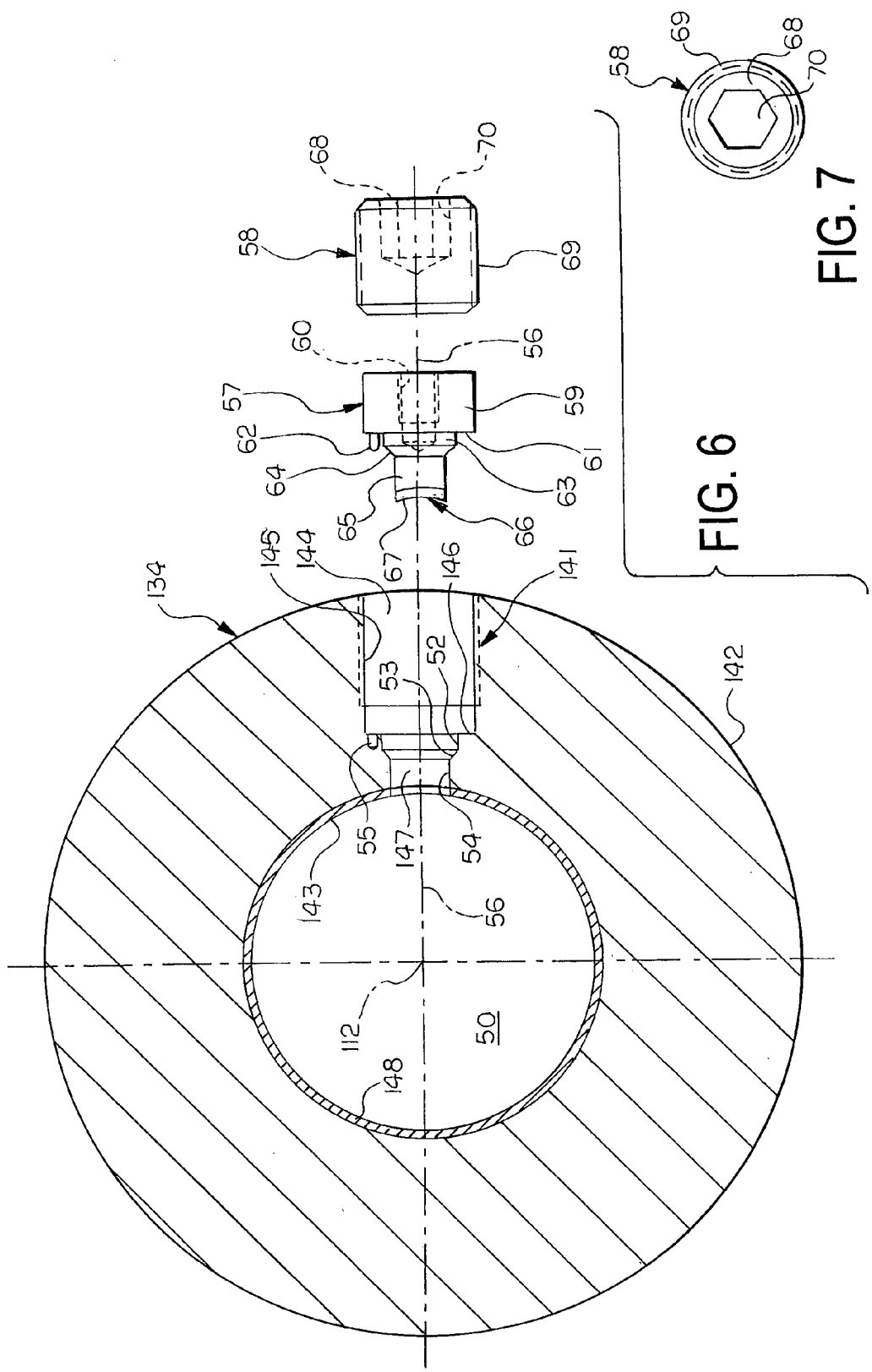

APPARATUS AND METHOD FOR DETERMINING FEEDSCREW AND BARREL WEAR

BACKGROUND OF THE INVENTION

The present invention relates generally to an apparatus and method for detecting wear in a material processing machine and, in particular, to an apparatus and method for determining the wear of feedscrew flights and adjacent barrel interior surfaces.

Typically, a barrel and feedscrew are used to mix and melt various materials used in extrusion, blowmolding and injection processes. For example, bulk plastic material is fed into an extruder, an injection molding machine or a blow molder through the barrel or cylinder utilizing a rotating helical screw. Such a machine is operated at an elevated temperature and if it is required to be shut down, the plastic material tends to solidify. Many plastic materials are highly abrasive and tend to wear the flights on the screw thereby widening the gap between the outer edge of the flights and the inner surface of the barrel or cylinder. Such a condition will tend to prevent the uniform free flow of material through the barrel thereby causing problems in the consistency of the plastic material. Other problems that can occur are galling in the barrel through adhesive wear or metal to metal contact and misalignment of the screw through excessive shear or deflection of the screw mechanism.

Previously, the only way to check the dimensional clearances in such a mechanism was to shut it down and remove the screw from the barrel. Since the plastic material would solidify, the screw and the barrel would have to be cleaned and the dimensions checked utilizing mechanical measuring devices. Then, the mechanism would have to be reassembled. Such a procedure tended to result in lost production time and did not completely eliminate the occasional breakdowns between regular measurements.

In the U.S. Pat. No. 4,604,251, there is shown an apparatus and method for checking the dimensional relationship between the screw flights and the inner diameter of a barrel or cylinder during the operation of the plastic material feed device. Utilizing the Foucault current or eddy method of detection, a probe is located in an aperture formed in the side of the barrel or cylinder. The end of the probe is positioned near the inner surface of the barrel or cylinder. The probe generates an electrical signal having a magnitude proportional to the distance between the outer edge of the flight on the screw and a sensing coil located in the probe. The probe output signal is sensed and converted to a digital distance display for use by the machine operator.

The magnitude of the signal can be scaled to generate a display number representing the actual measurement between the edge of the flight screw and the inside of the barrel or cylinder in English or metric units. The signal can be stored, selectively reset and two or more probe detection signals can be selectively displayed.

SUMMARY OF THE INVENTION

The present invention concerns an apparatus for determining wear of a feedscrew and barrel combination comprising: a barrel having a central bore extending along a longitudinal axis and a measuring aperture formed in a wall of the barrel, the measuring aperture extending along an axis radially from the longitudinal axis; a feedscrew rotatably positioned in the central bore; and a gage plug releasably retained in the measuring aperture, the gage plug having an inner end curved to correspond to a curvature of a surface of the central bore surrounding an inner end of the measuring aperture. The apparatus includes locating means for maintaining alignment of the gage plug inner end with the central bore surface during rotation of the feedscrew in the barrel. A retaining plug is releasably retained in the measuring aperture and prevents removal of the gage plug. The gage plug can have a cap at the inner end formed of a material having a wear rate corresponding to a wear rate of the central bore surface. A probe is releasably retained in the measuring aperture when the gage plug and the retaining plug are removed for determining wear of a flight of the feedscrew.

A method of determining wear of a feedscrew and barrel combination according to the present invention comprises the steps of: a) forming a measuring aperture in a barrel with a feedscrew rotatable in a central bore between an outer surface of the barrel and an inner surface at the central bore; b) providing a gage plug having an inner end with a curvature corresponding to a curvature of the inner surface of the barrel; c) inserting the gage plug in the measuring aperture and aligning the curvature of the inner end with the curvature of the inner surface; d) rotating the feedscrew and then stopping the rotation of the feedscrew; e) removing the gage plug from the measuring aperture; and f) determining a value of wear in the central bore of the barrel by determining a value of wear at the inner end of the gage plug. The method further includes a step of inserting a probe in the measuring aperture after performing step e) and operating the probe to determine a value of wear of a flight of the feedscrew. The method also can include a step of providing a test bar and substituting the test bar for the feedscrew in the barrel, inserting the probe in the measuring aperture and operating the probe to calibrate an output signal representing a value of simulated wear of a flight of the of the test bar.

DESCRIPTION OF THE DRAWINGS

The above, as well as other advantages of the present invention, will become readily apparent to those skilled in the art from the following detailed description of a preferred embodiment when considered in the light of the accompanying drawings in which:

FIG. 6 is a view similar to FIG. 5 with the feedscrew removed and showing a gage plug and a retainer plug in accordance with the present invention for insertion into the measuring aperture;

FIG. 7 is a top plan view of the retainer plug shown in FIG. 6;

DESCRIPTION OF THE PREFERRED EMBODIMENT

Figure 1:
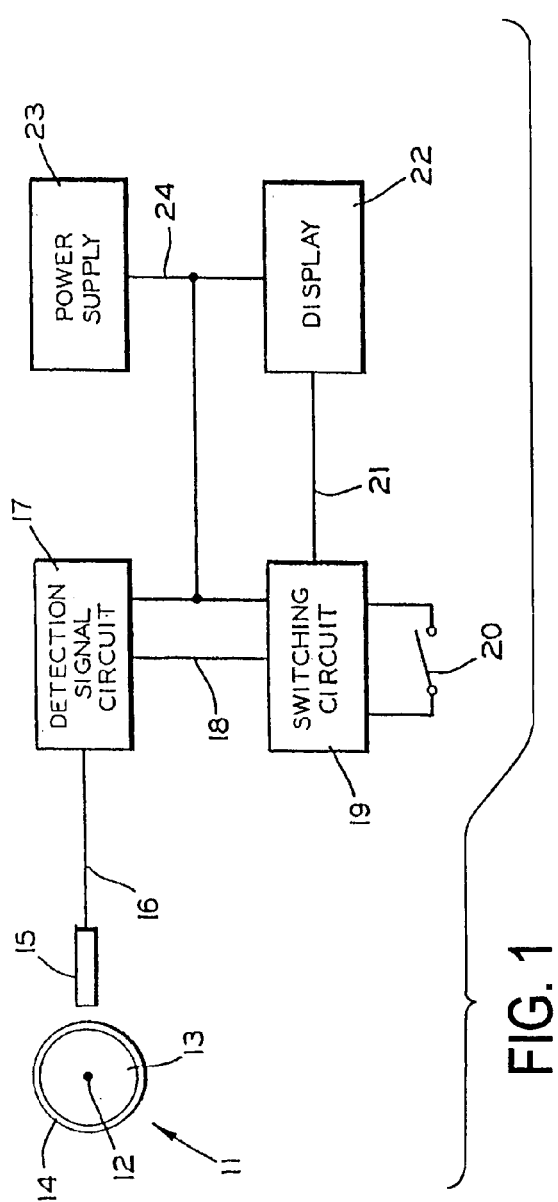
FIG. 1 is a schematic representation of a prior art apparatus for measuring displacement of a feedscrew.

There is shown in FIG. 1 a schematic block diagram of a prior art apparatus for detecting feedscrew wear or misalignment according as shown in the U.S. Pat. No. 4,604,251, which patent is incorporated herein by reference. A feedscrew 11 rotates about a longitudinal axis 12 thereof. The feedscrew 11 is formed of a generally cylindrical body 13 having a helical flight or thread 14 formed on an exterior surface of the body 13. A probe 15 is positioned adjacent the flight 14 to sense the distance between an end of the probe and an outer edge of the flight. The probe 15 generates a detection signal along a cable 16 to a detection signal circuit 17. The magnitude of the output signal generated by the detection signal circuit 17 on a line 18 is proportional to the distance between the end of the probe 15 and the outer edge of the flight 14.

The output signal on the line 18 is an input to a switching circuit 19. The switching circuit 19 incorporates a conventional signal holding circuit, which stores the magnitude of the signal on the line 18 at the time a reset switch 20 is closed. This stored signal is generated on a line 21 to a display circuit 22 whereby an indication of the distance between the probe and the flight is displayed as a number in a selected mode of measurement. Various conventional digital or analog displays could be utilized for the display 22, but a digital display in English or metric units is preferred. The probe 15, the circuits 17 and 19 and the display 22 are provided with electrical power by a power supply 23 on a line 24.

Figure 2:
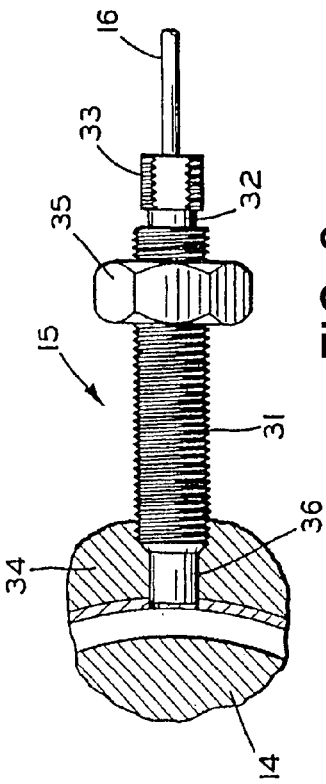
FIG. 2 is a plan view of the prior art probe shown in FIG. 1.

The probe 15 of FIG. 1 is shown in plan view in FIG. 2. The probe 15 has a generally cylindrical body with an externally threaded central portion 31. At one end of the probe 15 is a relatively short, narrower diameter portion 32 connecting the body portion 31 to a squared off head portion 33. The head portion 33 is adapted to be gripped by an open end or adjustable wrench, or similar tool for threading the body 31 into a threaded aperture in a wall of a barrel or cylinder 34. A nut 35 is threaded onto the body portion 31 and is utilized as a stop nut against an outer surface of the barrel 34 (not shown) or a spacer (not shown) positioned between the nut 35 and the outer surface of the barrel 34.

A sensor assembly 36 is positioned at an end of the probe body 31 opposite the head portion 33 and includes a wire coil (not shown) connected to the cable 16. The probe 15 has a bore (not shown) formed therein coextensive with the longitudinal axis of the body 31 to permit the connection of the coil with the cable 16.

Figure 3:
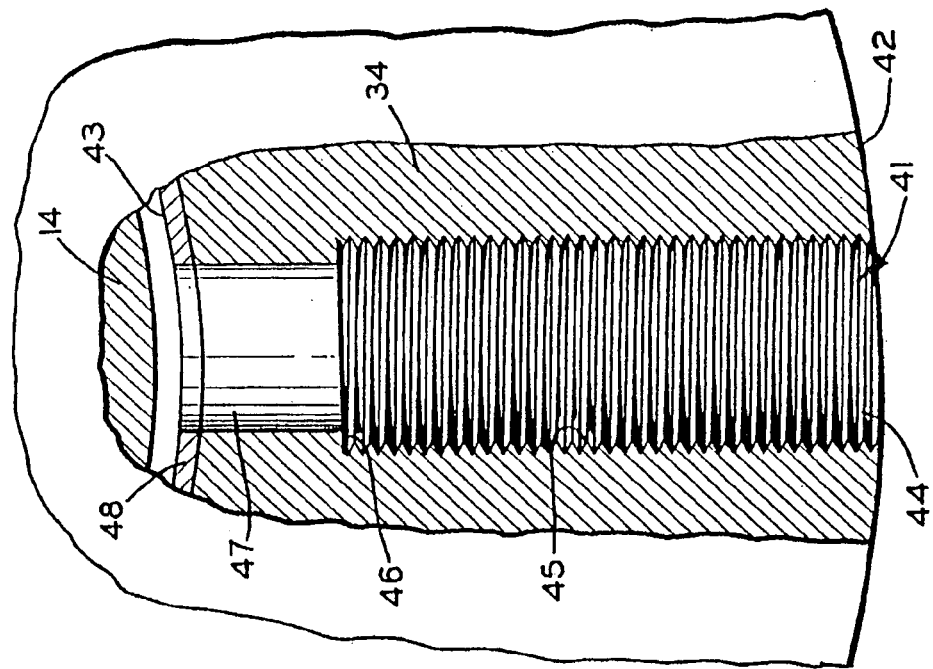
FIG. 3 is a fragmentary plan view taken as if in partial cross section through the screw and the barrel of FIGS. 1 and 2 showing an aperture formed to accept the probe.

There is shown in FIG. 3 a plan view of an extruder barrel and screw taken as if in partial cross-section. An aperture 41 is formed in the wall of the barrel 34 extending from an outer surface 42 to an inner surface 43 adjacent an outer edge of the flight 14 on the screw 11. The aperture 41 is formed with a larger diameter area 44, which is threaded its entire length as shown at 45, that terminates in a step surface 46. The aperture 41 then extends as a narrower diameter portion 47 from the step surface 46 to the inner surface 43 of the barrel 34 through an inner liner 48 of the barrel. The distance between the sensor assembly 36 shown in FIG. 2 and the outer surface of the flight of the screw is approximately 0.035 inch to 0.040 inch.

As the probe 15 is threaded into the aperture 41, the one end of the threaded section 31 comes into contact with the step surface 46 which functions as a stop to position the probe with the sensing end 36 in the proper position for sensing the distance between the probe end and the outer edge of the flight 14. When data retrieval is completed, the probe 15 is removed from the aperture 14. Typically, the probe 15 is removed and the aperture sealed during regular manufacturing operations to prevent material leakage or damage to the probe 15. A plug (not shown) may be used to seal the aperture 41 when the probe is not in use and removed.

FIGS. 4–8 show the apparatus and method for detecting wear according to the present invention. Components shown in FIGS. 4–8 that are similar to the components shown in FIGS. 1–3 are identified by the same reference numeral with "100" added. Thus, the feedscrew 11 shown in FIG. 1 corresponds to a feedscrew 111 shown in FIG. 4.

Figure 4:
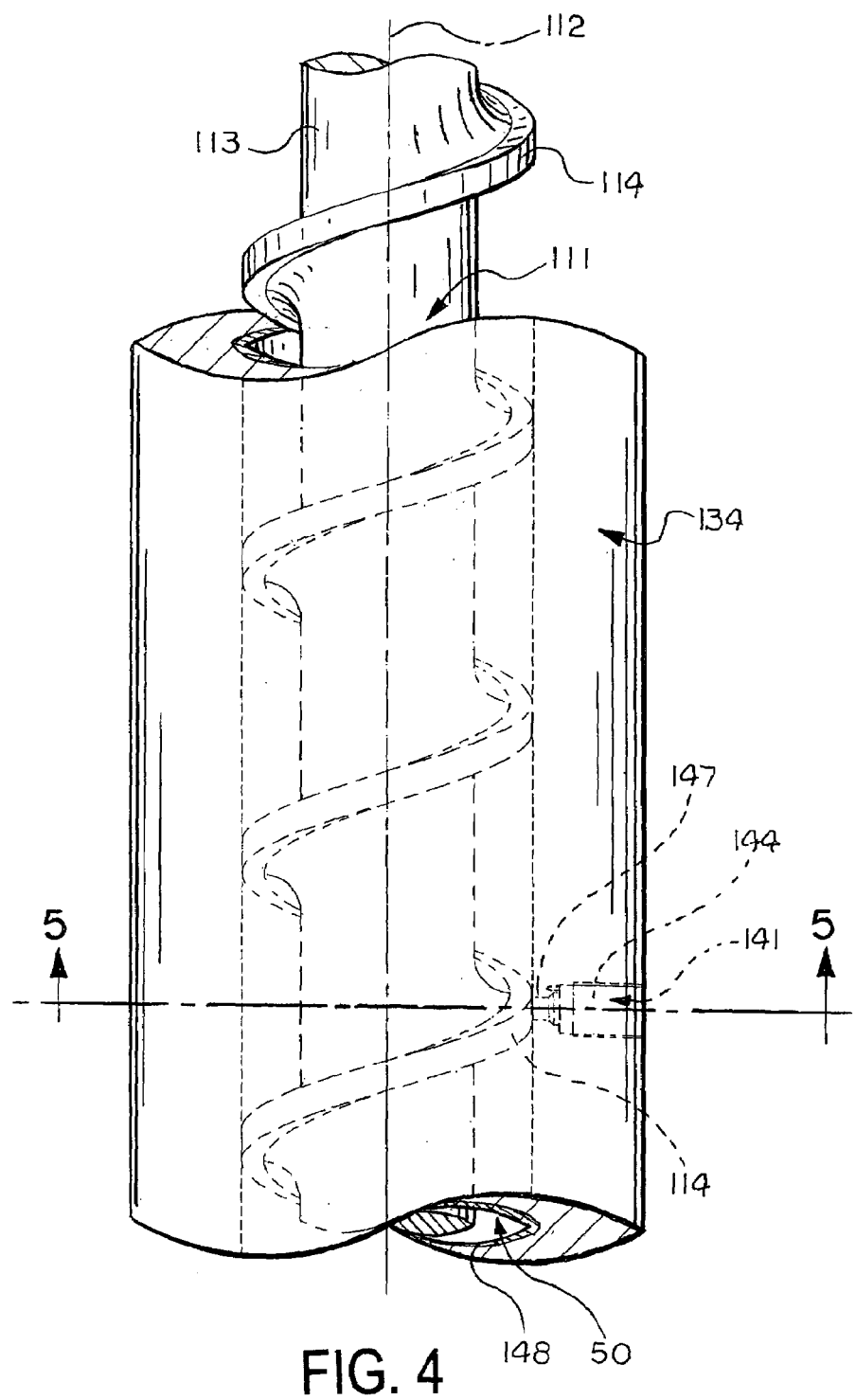
FIG. 4 is a fragmentary plan view of a barrel and feedscrew illustrating a measuring aperture formed in the barrel wall in accordance with the present invention.

FIG. 4 is a fragmentary plan view of a barrel 134 and the feedscrew 111 with which the apparatus and method for detecting wear according to the present invention can be used. The feedscrew 111 extends along a longitudinal axis 112 as a cylindrical body 113 with a helical flight 114 formed on an exterior thereof. The barrel 134 also extends along the axis 112 and has a central bore 50 in which the feedscrew 111 is positioned for rotation. A wall of the central bore 50 can be covered by a liner or coating 148 used to reduce wear caused by the material passing through the barrel 134. Typically, the liner or coating 148 is formed of a material that is more abrasion resistant than the material from which the barrel 134 is formed. The feedscrew 111 and the barrel 134 are of conventional construction and are available from Glycon of Tecumseh, Mich.

Figure 5:
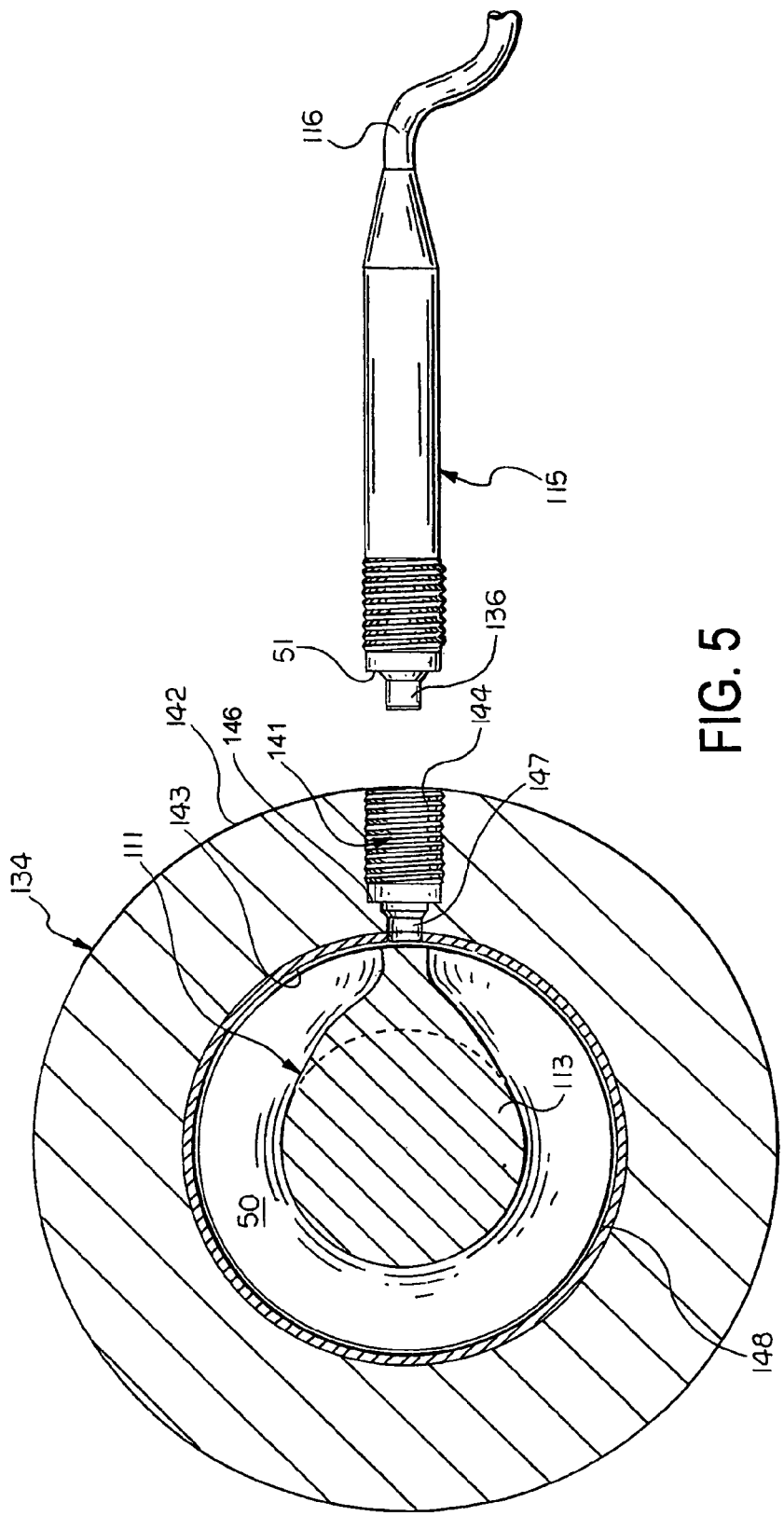
FIG. 5 is an enlarged cross-sectional view taken along the line 5—5 in FIG. 4 showing a probe for insertion into the measuring aperture.

The apparatus and method according to the present invention involves forming a measuring aperture 141 through the wall of the barrel 134 and the liner or coating 148. The aperture 141 extends radially relative to the axis 112 from an outer surface 142 of the barrel 134 to an inner surface of the liner or coating 148 as shown in FIGS. 4–6. Extending inwardly from the outer surface 142, the aperture 141 has a larger diameter portion 144 that is at least partially threaded 145. Extending outwardly from the inner surface 143, the aperture 141 has a smaller diameter portion 147 that joins the larger diameter portion 144 at a step 146.

As shown in FIG. 5, a probe 115 is configured for insertion into the aperture 141. The probe includes a sensor 136 at one end and a cable 116 to carry power to and signals from the sensor 136. A shoulder 51 is formed on the probe 115 for engaging the step surface 146 thereby spacing the sensor 136 a predetermined distance from the axis 112 each time the probe is inserted into the aperture 141. The probe 115 can use any known type of proximity detection technology. The detection signal generated by the probe 115 can be input to a signal processing and display unit 3 such as a Hocking "Locator 2" handheld eddy current inspection unit or a Hocking "Phasec 2" eddy current inspection unit, both available from GE inspection Technologies, LP of Lewistown, Pa.

As best seen in FIG. 6, the smaller diameter portion 147 is formed in three sections 52, 53 and 54. The outer section 52 extends inwardly from the step surface 146 and is cylindrical. The intermediate section 53 tapers from a larger diameter of the outer section 52 to a smaller diameter of the inner section 54. The inner section 54 is cylindrical and opens through the liner or coating 148 to the barrel central bore 50. A locator recess 55 is formed in the step surface 146 and extends generally parallel to an axis 56 of the aperture that intersects the longitudinal axis 112 of the barrel 134.

When the probe 115 is not positioned in the aperture 141 for measuring wear on the flight 11.4 of the feedscrew 111., the aperture is closed by a barrel wear detector, in the form of a gage plug 57, and a retainer or retaining plug 58. The gage plug 57 has a cylindrical body 59 with a recess 60 formed in an outer end surface for receiving a tool (not shown) to aid in positioning the gage plug 57 in the aperture 141. An inner end surface of the body forms a shoulder 61 from which a pin 62 extends. The pin 62 is spaced from the central axis of the body so as to be received in the recess 55 and a tool in the recess 60 can be used to rotate the gage plug 57 to align the pin 62 with the recess 55. Extending axially inwardly from the body 59 is a plug outer section 63 corresponding to the aperture outer section 52, a plug intermediate section 64 corresponding to the aperture intermediate section 53 and a plug inner section 65 corresponding to the aperture inner section 54. An inwardly facing end 66 of the inner section 65 is curved to correspond to the curvature of the inner surface 143 of the barrel 134 and includes a cap 67 formed of the same material as the liner or coating 148. The distance from the shoulder 61 to the end 66 is the same as the distance from the step surface 146 to the inner surface of the liner or coating 148. The recess 55 cooperates with the pin 62 to align the curvature of the cap 67 with the curvature of the inner surface 143 so that the cap 67 will wear at the same rate as the liner or coating 148. Therefore, the length of the gage plug 57 provides an indication of the wear on the inner surface 143 of the barrel 134. However, means fox aligning other than the recess 55 and the pin 62 can be used.

The gage plug 57 is held in the aperture 141 by the retaining plug 58. As shown in FIGS. 6 and 7, the retaining plug 58 has a cylindrical body 68 that is externally threaded 69. The body 68 has a recess 70 formed in an outer end for receiving a tool (not shown) for rotating the threads 69 into engagement with the threads 145 in the aperture 141. The retaining plug 58 is rotated into contact with the gage plug 57 to seat the plug intermediate section 64 against the aperture intermediate section 53 and securely close the aperture 141.

As stated above, to assure that the gage plug 57 wears equally and uniformly to that of the inner surface 143 of the barrel 134, the gage plug 57 is produced using the same material layered composition as the wall of the barrel 134. For example, a typical barrel is produced from two different materials to form a bimetallic cylinder. An outer cylinder is typically manufactured from a common mill metal such as a suitable steel. The liner or coating 148 is commonly formed from an alloy that is produced by a spin cast operation to form a cast liner (i.e., inner surface lining). The typical liner 148 has a wall thickness at least 0.050 inch thick. The liner 148 is manufactured for high-performance operations. Various alloys, such as those available from bimetallic cylinder manufacturer Wexco Corporation of Lynchburg, Va, can be used for effectively operating under special environmental conditions, such as abrasive and/or corrosive environments. Furthermore, different lining thicknesses can be used for specific applications to increase longevity of the barrel 134. The outer cylinder and the liner are adhered utilizing a fusing process. Alternatively, other types of adjoining processes may be used.

To maintain the same wear rate as the liner 148 of the barrel 134, the gage plug 57 can be manufactured using the same material and thickness for the cap 67. However, the cap 67 could be formed of a different material and thickness that will result in the same wear characteristics. Also, the cap 67 could be eliminated and the entire gage plug 57 could be formed of the same or a different material.

Figure 8:
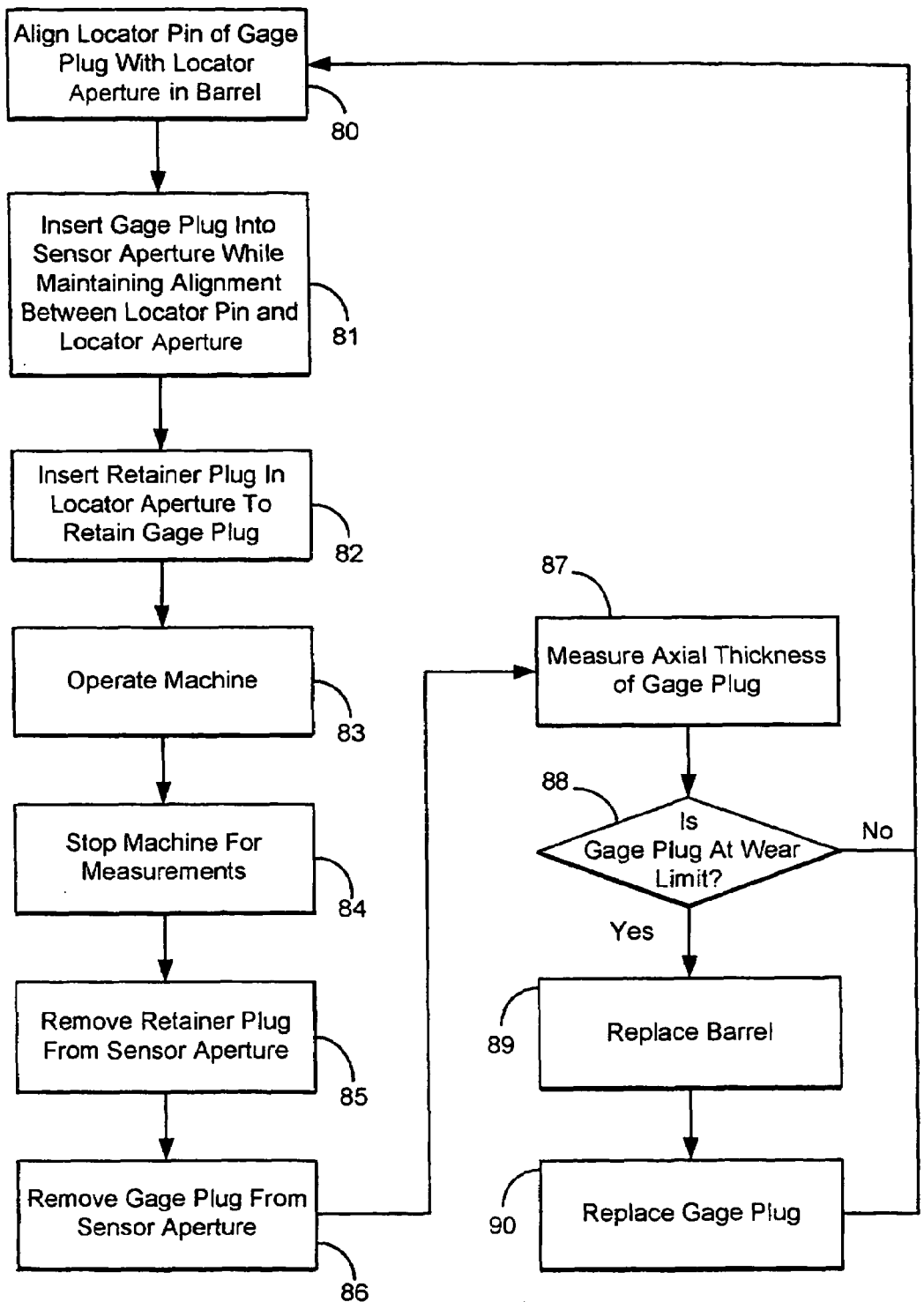
FIG. 8 is a flow diagram of a method for determining barrel wall wear according to the present invention.

FIG. 8 illustrates a method according to the present invention for determining the wear of the wall of the barrel 134 without having to disassemble the barrel. As shown in FIGS. 4–6, first the measuring aperture 141 with the recess 55 is formed in the wall of the barrel 134 and the gage plug 57 and the retaining plug 58 are provided. In a step 80, the gage plug pin 62 is aligned with the locator recess 55. The gage plug 57 is orientated so as to align the curvature of the cap 67 with the curvature of the liner 148. In a step 81, gage plug 57 is inserted into the aperture 141 while maintaining an alignment between the locator pin 62 and the locator recess 55. If the locator pin 62 does not seat within the locator recess 55, the gage plug 57 is rotated until the locator pin 62 is fully seated. The steps 80 and 81 can be combined by inserting the gage plug 57 in the aperture 141 and rotating, if necessary, to seat the pin 62 in the recess 55.

In a step 82, the retaining plug 58 is inserted into the aperture 141 thereby retaining the gage plug 57. In the preferred embodbnent, the threads 69 on the retainer plug engage the threads 145 on the wall of the aperture 141 and the retaining plug 58 is rotated into place. Other methods of retention may be used 3 such a keyed lock-down feature. In a step 83, the machine including the feedscrew 111 and the barrel 134 is cycled to perform manufacturing operations. At predetermined inspection intervals or any other time period, the manufacturing operation is stopped to inspect the barrel in a step 84. The retainer plug 58 is disengaged and removed from the aperture 141 in a step 85. In a step 86, the gage plug 57 is removed from the aperture 141.

In a step 87, the axial thickness of the gage plug 57 is measured. In the preferred embodiment, micrometers are used to measure the gage plug, however, any suitable measuring device may be used to measure and inspect the wear of the gage plug 57. In other preferred embodiments, measurements other than the axial thickness or other types of measurement characteristics may be used in determining the wear characteristics of the gage plug 57. In a step 88, a determination is made whether the gage plug 57 has reached or exceeded a wear limit. If a determination is made in the step 88 that the gage plug 57 has not reached or exceeded the wear limit, then a branch is made at "No" and a return is made to the step 80 to re-insert the gage plug 57 into the barrel wall aperture 141. If a determination is made that the gage plug 57 is at or has exceeded the wear limit, then the barrel 134 is removed and replaced in a step 89. In a step 90, the gage plug 57 is replaced with a new gage plug and a return is made to the step 80 to insert the new gage plug in the new barrel.

The apparatus and the method according to the present invention provide an accurate indication of feedscrew wear, barrel wear and/or misalignment between the feedscrew and the barrel during the operation of a material feeder. Such an indication tends to eliminate the regular shutdowns and disassembly for measurement previously required. Furthermore, the apparatus and method provide an early warning of a pending breakdown and indicate the right time for preventative maintenance or barrel changeover. Thus, both a barrel and a feedscrew can now be changed at the exact point in the operating life when the plasticizing rate drops off significantly. More than one measurement point can be provided with location and number of gage plug wear indicators determined by an analysis of the critical points in the particular feeder.

Figure 9:
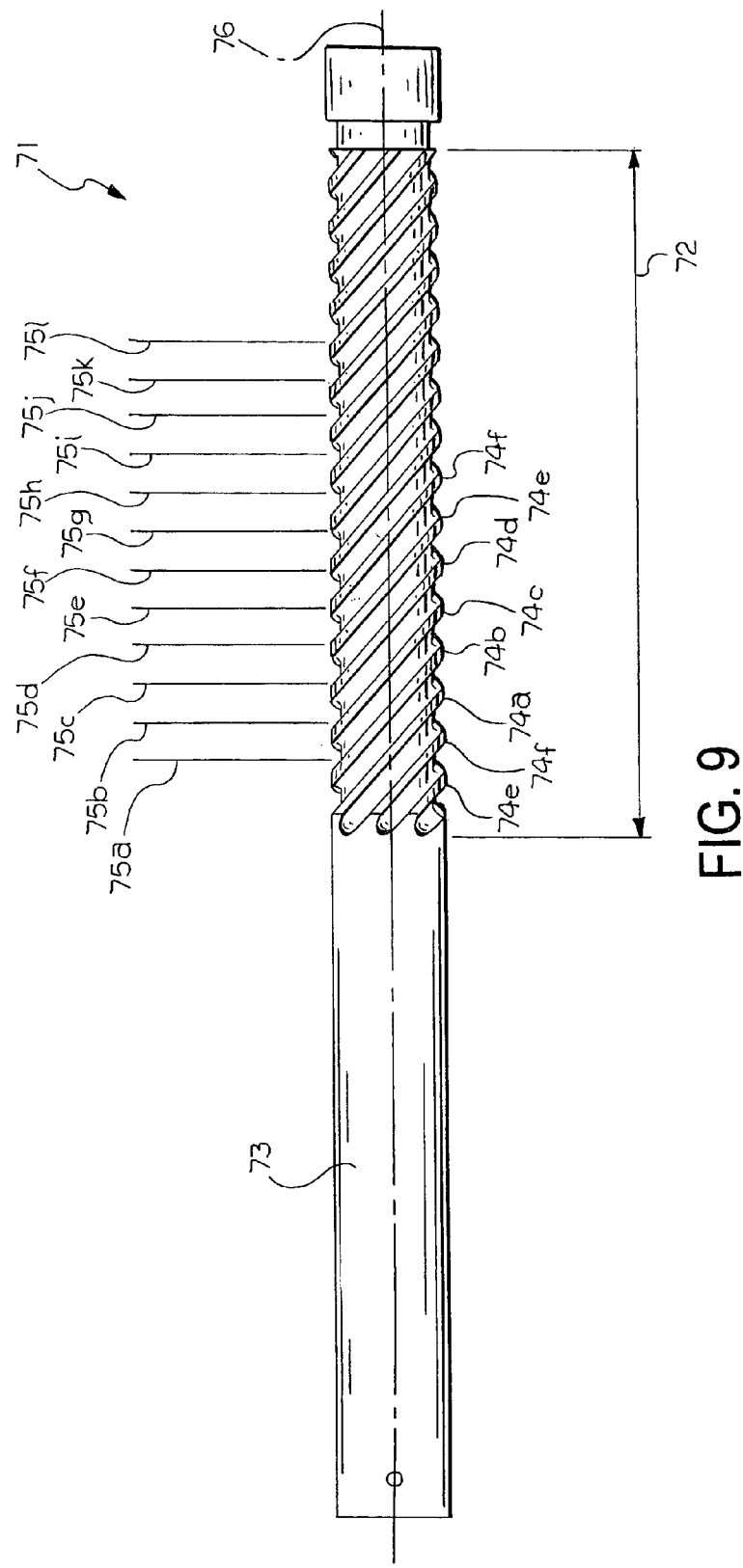
FIG. 9 is a plan view of a test bar according to the present invention.

There is shown in FIG. 9 a test bar 71 for calibrating the probe 115. The test bar 71 simulates a feedscrew and has a calibration section 72 attached to a constant diameter section 73. The constant diameter section 73 can have the diameter of an unworn flight of the feedscrew to be inspected. The calibration section 73 is formed with a plurality of flights that are stepped in diameter to simulate feedscrew wear. For example, the section 72 is formed with six flights 74athrough 74f that have a 6.75 inch lead. For the purposes of illustration, a plurality of planes 75a through 75l extend transverse to a longitudinal axis 76 of the test bar 71 at approximately one inch intervals. The test bar 71, can be formed of the same material as the feedscrew. In addition, feedscrew flights typically are "hardfaced" by applying a harder material to the surface to resist abrasion 1 such as a "Colmonoy 56" material available from Wall Colmonoy Corporation of Madison Heights, MI. Each of the flights 74a through 74f can be "hardfaced" with a different material to simulate actual feedscrew construction, To the left of the plane 75a, the constant diameter section 73 and the left end of each of the flights 74a through 74f can have a diameter of three inches which simulates no wear. In the area between the planes 75a and 75b, the flights can have a diameter of 2.990 inches which simulates a flight wear of 0.005 inch at diametrically opposed "sides" of the test bar 71. In the area between the planes 75b and 75c, the flights can have a diameter of 2.980 inches which simulates a flight wear of 0.010 inch at diametrically opposed "sides" of the test bar 71. The diameter of the flights can be reduced in a similar manner from left to right until the area to the right of the plane 75l has a diameter of 2.880 inches which simulates a flight wear of 0.060 inch at diametrically opposed "sides" of the test bar 71.

In operation, with the probe 115 installed in the measuring aperture 141 and the test bar 71 inserted in the central bore 50 of the berrel 134, the test bar can be moved longitudinally to position a selected one of the areas of the calibration section 73 adjacent to the measuring aperture 141. Then, the test bar 71 is rotated to generate a signal from the probe 115 that corresponds to a known diameter of the test bar 71.

Figures 10A, 10B:
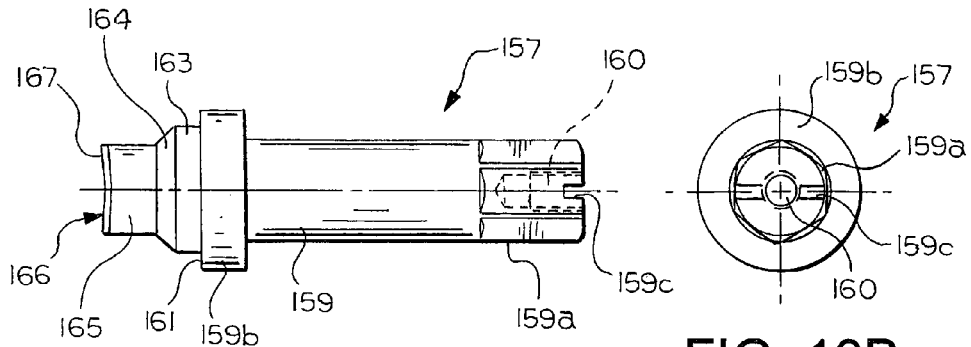
FIG. 10A is an elevation view and FIG. 10B is a top plan view of an alternate embodiment gage plug according to the present invention.

There is shown in FIGS. 10A and 10B an alternate embodiment gage plug 157 having a cylindrical body 159 with a threaded recess 160 formed in an outer end surface for receiving a tool (not shown) to aid in removing the gage plug 157 from an aperture in the feedscrew barrel wall. The body 159 has a top end portion 159a with a hexagonal outer surface sized for a standard open end wrench (not shown) of suitable size to rotate the gage plug 157. At an inner end of the body 159 there is formed a radially extending flange 159b having a shoulder 161 facing away from the top end 159a. A slot 159c extends transverse to a central axis of the body 159 at the opening of the recess 160 to receive a pin 172 (FIGS. 12A and 12B) that can be used when the gage plug 157 is installed in the feedscrew barrel to align the curvature of the plug end with the curvature of the inner surface of the barrel. Extending axially inwardly from the flange 159b is a plug outer section 163, a plug intermediate section 164 and a plug inner section 165. An inwardly facing end 166 of the inner section 165 is curved to correspond to the curvature of the inner surface of the barrel and includes a cap 167 formed of the same material as the liner or coating of the barrel.

Figures 11A, 11B:
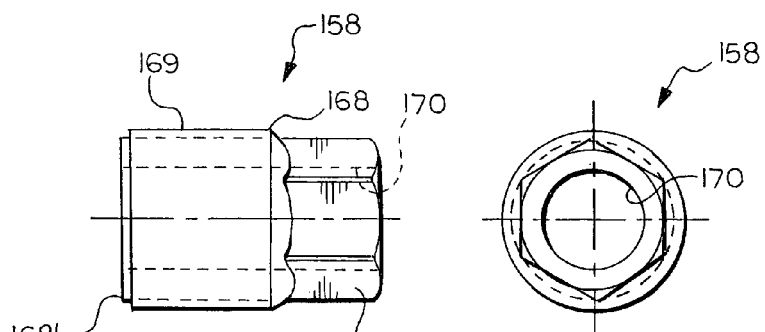
FIG. 11A is an elevation view and FIG. 11B is a top plan view of an alternate embodiment retaining plug according to the present invention.

There is shown in FIGS. 11A and 11B an alternate embodiment retaining plug 158 for holding the gage plug 157 in an aperture in the barrel wall. The retaining plug 158 has a cylindrical body 168 that is externally threaded 169 at one end and has a top end portion 168a with a hexagonal outer surface sized for a standard socket wrench (not shown) of suitable size for rotating the threads 169 into engagement with threads in the aperture in the barrel wall. The body 168 has a through aperture 170 extending along a central axis for receiving the central portion of the gage plug body 159. The retaining plug 158 is threaded into contact with the gage plug 157 to abut an end surface 168b against the gage plug flange 159b and seat the plug intermediate section 164 against the aperture intermediate section 53.

Figures 12A, 12B:
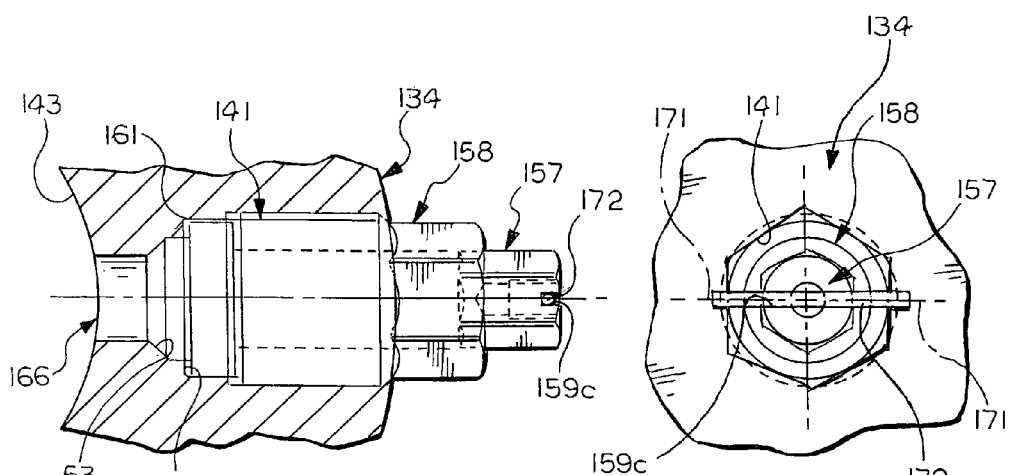
FIG. 12A is a cross-sectional view and FIG. 12B is a top plan view showing the gage plug of FIGS. 10A and 10B and the retaining plug of FIGS. 11A and 11B installed in a feedscrew barrel.

The gage plug 157 and the retaining plug 158 are shown installed in the barrel aperture 141 in FIGS. 12A and 12B. The gage plug 157 is inserted into the aperture with the shoulder 161 abutting the step surface 146. Then, the retaining plug 158 is threaded into the aperture 141 to hold the gage plug 157 in place. The pin 172 inserted in the slot 159c is aligned with one or more of a mark or alignment indicia 171 on the outer surface of the barrel 134 to position the curved end 166 such that its curved surface blends with the curved surface of the barrel inner surface 143. The pin 172 can be of any suitable cross sections such as round, square, rectangular, In accordance with the provisions of the patent statutes, the present invention has been described in what is considered to represent its preferred embodiment. However, it should be noted that the invention can be practiced otherwise than as specifically illustrated and described without departing from its spirit or scope.

What is claimed is:

1. An apparatus for determining wear of a feedscrew and barrel combination comprising:
   a barrel having a central bore extending along a longitudinal axis and a measuring aperture farmed in a wall of said barrel, said measuring aperture extending along an axis radially from said longitudinal axis;
   a feedscrew rotatably positioned in said central bore; and
   a gage plug releasably retained in said measuring aperture, said gage plug having an inner end curved to correspond to a curvature of a surface of said central bore surrounding an inner end of said measuring aperture, said inner end being aligned with an opening of said measuring aperture for indicating a wear of said surrounding central bore surface.

2. The apparatus according to claim 1 including locating means for maintaining alignment of said gage plug inner end with said central bore surface during rotation of said feedscrew in said barrel.

3. The apparatus according to claim 2 wherein said locating means includes a locating recess formed in said measuring aperture and said gage plug includes a pin releasably received in said locating recess.

4. The apparatus according to claim 2 wherein said locating means includes at least one alignment indicia on an outer surface of said barrel adjacent said measuring aperture and said gage plug includes a slot fanned in an end surface and a pin removably retained in said slot for alignment with said a: least one alignment indicia.

5. The apparatus according to claim 1 wherein said measuring aperture includes a step surface and said gage plug includes a shoulder engaging said step surface.

6. The apparatus according to claim 1 including a retaining plug releasably retained In said measuring aperture and preventing removal of said gage plug.

7. The apparatus according to claim 6 wherein said measuring aperture has first threads tanned on a wall therein and engaging second threads toned on an exterior of said retaining plug.

8. The apparatus according to claim 6 wherein said retaining plug has a tool receiving recess fanned in an outer end thereof.

9. The apparatus according to claim 6 wherein said retaining plug has a tool receiving outer surface for removing said retaining plug from said measuring aperture.

10. The apparatus according to claim 6 including a probe releasably retained in said measuring aperture when said gage plug and said retaining plug are removed for determining wear of a flight of said feedscrew.

11. The apparatus according to claim 1 wherein said gage plug has a cap at said inner end formed of a material having a wear rate corresponding to a wear rate of said central bore surface.

12. A method of determining wear of a feedscrew and barrel combination comprising the steps of:
 a) forming a measuring aperture in a barrel with a feedscrew rotatable in a central bore between an outer surface of the barrel and an inner surface at the central bore;
 b) providing a gage plug having an inner end with a curvature corresponding to a curvature of the inner surface of the barrel;
 c) inserting the gage plug in the measuring aperture and aligning the curvature of the inner end with the curvature at the inner surface;
 d) rotating the feedscrew and then stopping the rotation of the feedscrew;
 e) removing the gage plug from the measuring aperture; and
 f) determining a value of wear in the central bore of the barrel by determining a value of wear at the inner end of the gage plug.

13. The method according to claim 12 including a step of inserting a retaining plug in the measuring aperture before performing said step d) and a step of removing the retaining plug before performing said step e).

14. The method according to claim 12 including providing the gage plug with a cap at the inner end formed of a material having a wear characteristic corresponding to a wear characteristic of the inner surface of the central bore.

15. The method according to claim 12 including a step of inserting a probe in the measuring aperture after performing said step e) and operating the probe to determine a value of wear of a flight of the feedscrew.

16. The method according to claim 15 including a step of providing a test bar and substituting the test bar for the feedscrew in the barrel, inserting the probe in the measuring aperture and operating the probe to calibrate an output signal representing a value of simulated wear of a flight of the test bar.

* * * * *